Figure 3:
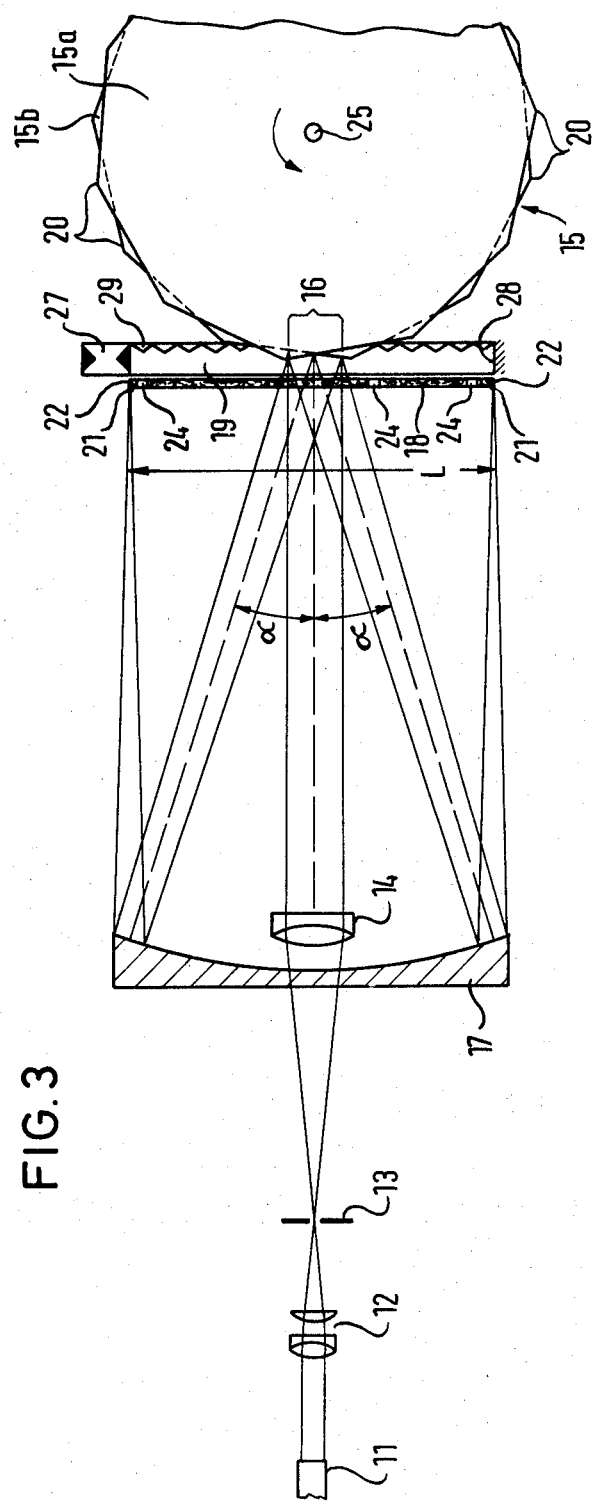

United States Patent [19]

Sick et al.

[11] 4,291,987

[45] Sep. 29, 1981

[54] HOLE SEEKING APPARATUS

[75] Inventors: Erwin Sick, Icking; Siegfried Mankel, Geretsried, both of Fed. Rep. of Germany

[73] Assignee: Erwin Sick GmbH, Optik-Elektronik, Fed. Rep. of Germany

[21] Appl. No.: 114,591

[22] Filed: Jan. 23, 1980

[30] Foreign Application Priority Data

Feb. 6, 1979 [DE] Fed. Rep. of Germany ....... 2904435

[51] Int. Cl.$^3$ ..................... G01N 21/89; G02B 27/17
[52] U.S. Cl. ...................................... 356/431; 350/6.8
[58] Field of Search .......................... 250/572; 350/6.8; 356/238, 431, 444

[56] References Cited

U.S. PATENT DOCUMENTS

| 2,844,648 | 7/1958 | Rosenthal | 350/6.8 |
| 3,488,102 | 1/1970 | Buck et al. | 350/6.8 |
| 3,646,568 | 2/1972 | Woywood | 350/6.8 |

*Primary Examiner*—John K. Corbin
*Assistant Examiner*—Bruce Y. Arnold

[57] ABSTRACT

Hole seeking apparatus for material webs is disclosed which features a light source for projecting a light beam onto a mirror wheel arrangement located optically in front of a concave mirror so as to produce a scanning beam in the image space of the concave mirror. The scanning beam is continuously displaced parallel to itself so as to periodically scan along a scanning path on the material web. The mirror wheel arrangement consists of two substantially identical mirror wheels which lie coaxially on one another and which are displaced by a half pitch.

The dimensions of the light bead at its point of incidence on the mirror wheels and the optical geometry of the apparatus are selected to avoid light being scattered at an edge of either of the mirror wheels and passing to either side of the web. Scattered light is thus prevented from falling on a light receiving device arranged behind the web and intended to detect the presence of holes therein. In this way the false recognition of a hole at the margins of the web is prevented.

8 Claims, 3 Drawing Figures

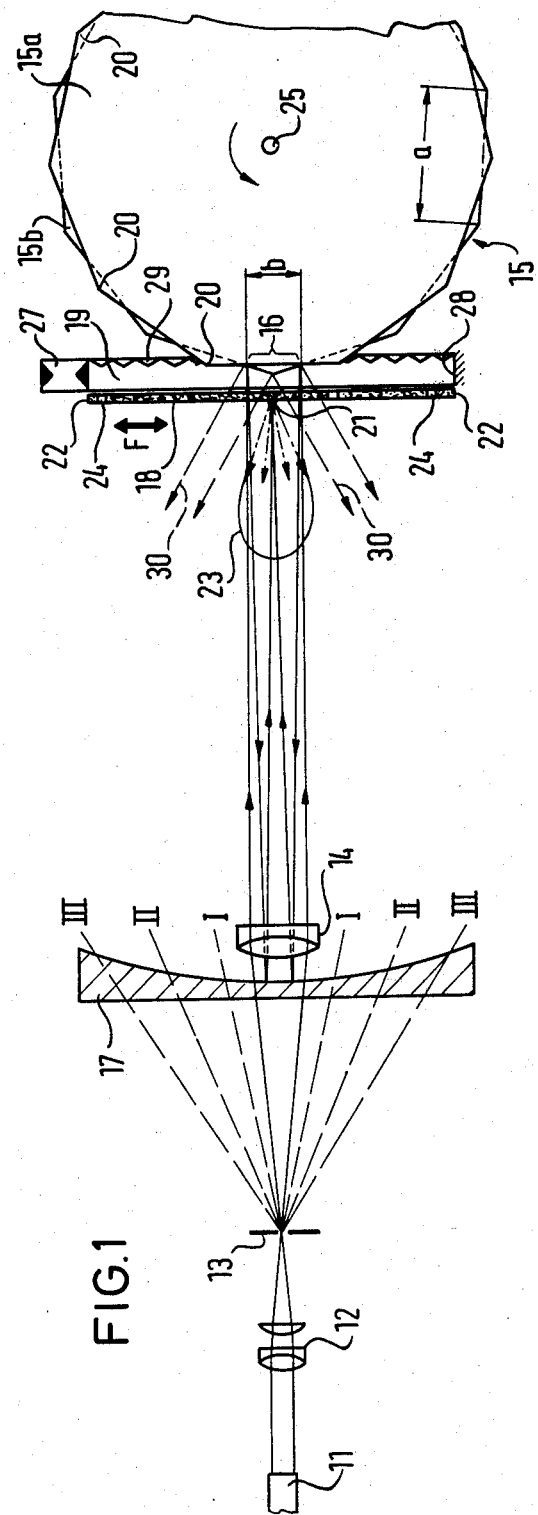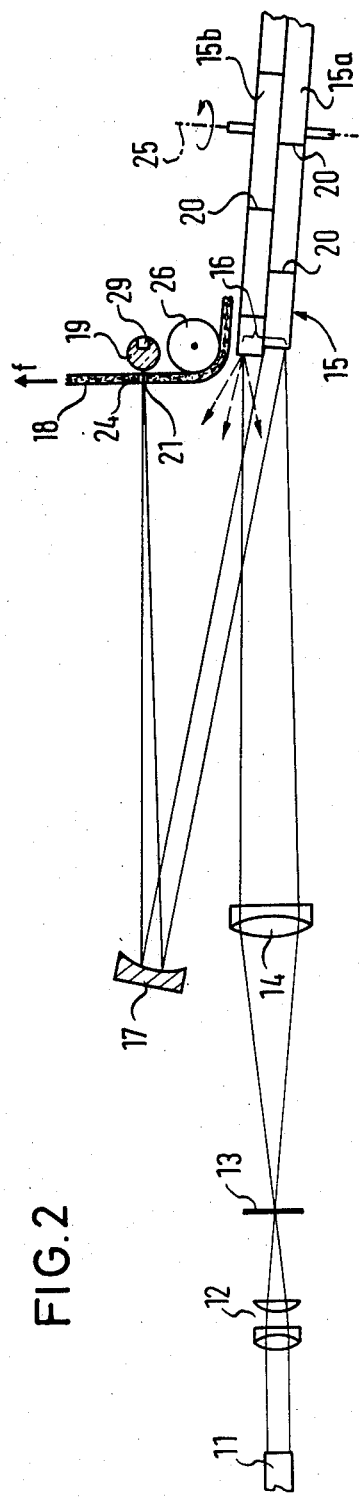

HOLE SEEKING APPARATUS

The invention relates to hole seeking apparatus for detecting holes in leaf like material, in particular, in moving material webs.

Apparatus of this kind is known and generally features a light source, preferably in the form of a laser, a microobjective which concentrates the laser light on the slot of a slot aperture, an objective which generates a light bead on a mirror wheel the rotational axis of which extends substantially parallel to the slot of the slot aperture and the surface of which is located generally at the focal point of a strip-like concave mirror. The strip-like concave mirror receives light reflected at various angles from the mirror wheel and produces a scanning beam which is continuously displaced parallel to itself in the image space of the concave mirror. The arrangement is such that the objective and concave mirror cooperate to image the slot aperture on the material web so that the material web is scanned point by point linewise by the scanning beam. The web speed is chosen during this movement to be such that every point of the web surface is monitored by the scanning beam. A light receiving arrangement is disposed behind the material web so that light passing through a hole in the web is detected and shows the presence of a hole therein.

The light receiving device generally takes the form of a light conducting rod which extends parallel to the path of the scanning light bead on the web and which has a photoelectric detector located at one of its endfaces with the other endface either reflecting or likewise having a photoelectric detector.

If the otherwise light impermeable web has a hole then, during scanning of the scanning light bead over the hole, light will pass through the web onto the surface of the light conducting rod and into its interior whereupon in known manner it will be conducted by total internal reflection to the photoelectric detector or detectors. An electronic processing circuit connected to the photoelectric detector thus provides a signal when the scanning light bead sweeps over a hole in the web. The web itself moves in a plane right at angles to the path of the scanning bead with a speed such that, as previously mentioned, the scanning light bead monitors the entire web surface by virtue of its continuously repeating scanning cycle.

A problem with hole seeking apparatus of this kind is that light is periodically scattered at the edges between two plane facets of the mirror wheel within a "scattering lobe" in directions which deviate from the directions of reflection of the neighbouring mirror facets. This is precisely the situation which occurs when the mirror wheel is at an angular position at which the scanning light bead falls on the margins of the web. Thus, as a result of the extent of the scattering lobe, a halo caused by scattering at the edge is present around the actual scanning light bead which signifies that a certain quantity of light will pass sideways past the edge of the web and will reach the light receiving arrangement. For tolerance reasons the latter will extend beyond the web and thus the danger arises that on scanning the web in the vicinity of its margins an error signal will be triggered although no hole is actually present at the edge of the web.

The principal object underlying the present invention is thus to provide hole seeking apparatus of the kind previously mentioned in which this disadvantage is avoided and scattered light originating from the edges of the mirror wheel are avoided when scanning the web in the vicinity of its two margins. For accomplishing this object the invention envisages that the mirror wheel comprises first and second substantially indentically constructed mirror wheels which lie coaxially one on the other and which are displaced by a half pitch of a facet relative to one another, that the light bead embraces both mirror wheels and has a smaller extent in the peripheral direction than the half peripheral length of a mirror fact and that the maximum length of the path of the scanning light bead is determined by that maximum angle of reflection of the light beam on the facets of the mirror wheels at which the light bead contacts no edges of the mirror wheels.

In this manner there is achieved, on the one hand, an uninterrupted sequence of scanning cycles without light falling on one of the edges of the two mirror wheels during scanning of the two edges of the web. On the contrary the light bead which is present on the mirror wheels during scanning of the web in the vicinity of its margins is exclusively located inside the plane mirror surface between the edges. Scattered light from the edges is therefore not able to occur in this region of the scanning cycle. It is indeed true that the edges of one or other of the mirror wheels enters the light bead, or the light beam which generates the light bead, during scanning of the web but this however occurs when the scanning light bead is at a safe distance from the margins of the web so that stray light generated from these edges is only able to reach regions of the material web and does not pass by the margins of the web which are located a safe distance away. The scattered light is thus kept away from the light receiving device unless a hole should be present in a portion of the web on which scattered light is able to fall. In this case however the fault signal initiated by scattered light passing through the hole can only be regarded as desirable.

Thus, in accordance with the invention, the construction is preferably so arranged that the light bead has an extent in the peripheral direction such that it only contacts an edge of the mirror wheel when the scanning light bead on the web has a distance from the edge of the web which lies outside of the scattering lobe due to the edge.

A further advantage of the construction of the mirror wheel as a double mirror wheel in accordance with the invention resides in the fact that double the number of mirror surfaces are effectively achieved without the need to increase the diameter and rotational speed of the mirror wheel. Thus, by virtue of the arrangement in accordance with the invention, a very compact construction is achieved and the centrifugal loading on the mirror wheel is reduced.

The problems described above in connection with the light passing the edges of the web could conceivably be decreased by modifying the size of the facets of a single mirror wheel; this, however, would mean that scanning could no longer be continuous and this would be quite unacceptable because large portions of the web would pass through the system unmonitored in the intervals between successive scanning cycles.

The light receiving arrangement is preferably a light conducting rod which extends transversely across the web. If desired a cylindrical lens can be interposed between the light receiving arrangement and the web to improve the optical conditions at the light conducting rod. The cross-section of the light conducting rod should then preferably be round. It is especially advantageous if the light conducting rod has a stepped mirror arrangement at its surface diametrically opposite to the light entry surface. In this way it is ensured that light which enters in a radial direction or in radial planes is reflected along the light conducting rod at angles of total internal reflection. A light conducting rod of this kind is for example described in German Offenlegungsschrift DE-OS No. 25 08 366.

A further problem of hole seeking apparatus of this kind resides in the fact that the light bead generated on the mirror wheel is not sharp and is blurred by diffraction images which extend around the light bead. These can extend sufficiently far that contacting of the edges of the mirror wheel cannot be avoided even when the light bead is itself made very small.

A further principal object of the invention thus resides in generating a light bead on the mirror wheel which has an exact geometry in particular in relation to its width in the peripheral direction. For accomplishing this further task the invention envisages that the slot aperture is a modal aperture stop which solely allows the zero order to reach the objective and which masks out all other orders. Such modal aperture stops are also frequently designated in German as "Ortsfrequenzfilter". Their apertures lie in the order of magnitude of a multiple of the wave length of the preferably used coherent light so that a diffraction figure is generated at the location of the objective the zero order of which just fills the objective. The remaining orders then pass the objective and, in accordance with the invention, are not used in the beam path of the hole seeking apparatus.

In this manner a sharply defined light bead arises on the surface of the mirror wheel which can be particularly well arranged in the above described manner inside the mirror wheel surfaces or facets so that, on scanning of the margins of the web, no edge of either of the two mirror wheels is located inside the light bead.

Further objects and advantages of the proposed arrangements will become clear from the following specific description which is made by way of example only and with reference to the accompanying drawings in which are shown:

FIG. 1 a schematic plan view of a hole seeking apparatus in accordance with the present invention, FIG. 2 a partial section of the side view of the arrangement of FIG. 1 and FIG. 3 a view analogous to that of FIG. 1 and showing a somewhat different angular position of the mirror wheel arrangement.

The illustration in the accompanying drawings is purely schematic and should no way be regarded as being to scale. The choice of illustration has been made from the point of view that all elements of the hole seeking apparatus of the invention can be completely reproduced in two figures.

Turning now to FIGS. 1 and 2 light from a light source 11 is concentrated by a microobjective 12 on a slot-like modal aperture stop 13. The slot width of the modal aperture stop amounts for example to approximately 10 microns.

The modal aperture stop is located at the focal point of an objective 14 and generates at the location of the objective a diffraction image the zero order of which directly embraces the aperture of the objective. The first, second and third orders etc. go past the objective 14 and are for example absorbed by a suitably arranged intermediate wall which is, for the sake of simplicity, not shown. The objective 14 generates a light bead on the surface of a mirror wheel arrangement 15 the rotational axis of which extends parallel to the slot of the modal aperture stop 13.

As can be seen from FIG. 2 the mirror wheel arrangement is arranged somewhat inclined to the optical axis of the illuminating beam path so that the light reflected from the surface of the mirror wheel arrangement 15 reaches a spherically concave mirror 17 which is arranged alongside the objective 14 and which is of strip-like form. The concave mirror 17 together with the objective 14 images the slot aperture of the aperture stop 13 on the surface of a material web 18. The material web moves continuously at right angles to the plane of the drawing of FIG. 1 and in the direction of the arrow F of FIG. 2. The web transport and guide devices are not shown in detail; however, a deflection roller 26 can be seen from FIG. 2 and the arrangement of web transport devices is well-known in the art.

In accordance with the invention the mirror wheel arrangement 15 comprises two first and second substantially identical mirror wheels 15a, 15b which are coaxially arranged and lie closely together but which are however displaced in a peripheral direction by a half pitch relative to one another as seen from FIGS. 1 and 2. The two mirror wheels 15a, 15b are fixed on the rotational axle 25 and turn with the same angular velocity.

The light head projected onto the mirror wheel arrangement 15 is intended to illuminate the two mirror wheels 15a, 15b completely in the axial direction. In the peripheral direction the light bead 16 has a length b, as seen in FIG. 1, which is smaller than half the peripheral length a of a mirror facet of either of the two mirror wheels 15a, 15b.

A light conducting rod 19 is arranged behind the material web 18 parallel to the scanning direction and carries a stepped mirror arrangement at its surface remote from the material web. The light conducting rod has a photoelectric detector 27 at one of its endfaces and its other endface 28 is provided with a reflective coating 28.

The sharp scanning light bead 21 which is generated on the surface of the material web scans the material web 18 continuously and periodically in directly following cycles transversely to its direction of movement. The scanning direction is indicated by the double arrow F of FIG. 1.

The scanning light bead 21 moves from one of the positions that can be seen in FIG. 3 at the edge 22 of the web to the centre of the web (FIG. 1) and from there further to the other edge 22.

Holes 24 are shown at various positions in the web. If the scanning light bead 21 impinges on a hole of this kind then light passes through the web into the light conducting rod 19 and passes from there to the photoelectric detector 27. Each hole thus produces an electrical fault signal at the output of the photoelectric detector 27. The length of the scanning path is indicated in FIG. 3 by the letter L.

By virtue of the construction in accordance with the present teaching the light bead 16 does not touch any of the edges 20 of the mirror wheels 15a, 15b for the angular position of the mirror wheel arrangement 15 shown in FIG. 3. In this angular position the light reflected at the plane mirror surfaces or facets reaches the margins 22 of the web 18 via the concave mirror 17.

If the mirror wheel 15 is turned further from the position of FIG. 3 into the position of FIG. 1 then one of the edges 20 enters into the light bead 16; however, the scanning light bead 21 is now at a certain distance from the edges 22 of the web 18. The presence of the edge 20 in the light bead 16 gives rise to scattered light which is schematically reproduced by the scattering lobe 23 of FIG. 1. If however, in accordance with the invention, care is taken to ensure that this scattered light only arises when the scanning light bead is a sufficient distance from the edges 22 of the web, then the scattered light cannot pass the edges 22 of the web and this ensures that holes are reliably detected even in the vicinity of the margins of the web. The fact that the light bead 16 has an exactly defined geometrical form due to the masking out of all the higher order defraction images plays a significant roll in ensuring the reliability of the device.

Reflected light beams are illustrated at 30 in FIG. 1 which lie beyond the measuring range L and which thus in no way influence the detection of holes.

It will apparent to those skilled in the art that various modifications can be made to the arrangements herein described without departing from the scope of the present teaching.

We claim:

1. Hole seeking apparatus for detecting holes in material webs using optical beam scanning apparatus for cyclically scanning a light bead across a material web from one margin to the other, and a light receiving device disposed behind the web for detecting light transmitted through holes therein, said optical beam scanning apparatus comprising a light source, preferably in the form of a laser, a microobjective, a slot aperture on which light from said light source is concentrated by said laser, first and second substantially identically constructed mirror wheels rotatable about a common axis and having multiple facets, said first and second mirror wheels lying coaxially adjacent one another and being displaced by a half pitch of one facet relative to one another, an objective for directing light from said slot aperture towards said axis of rotation onto said facets to form a patch of light thereon and a strip-like concave mirror with its focus coincident with said patch of light to direct light reflected from said first and second mirror wheels onto said material web to form said light bead, with the width of said patch of light in the peripheral direction of the first and second mirror wheels being less than one half the peripheral length of a said facet and such that edges between the facets of the first and second mirror wheels first enter the patch of light when the light bead on the web is at a distance from the margin of the web such that light scattered from a said edge within the scattering lobe of the edge can no longer be reflected from said concave mirror past a margin of the material web.

2. Hole seeking apparatus in accordance with claim 1 and wherein said edges first enter said patch of light when said light bead has a distance from the margin of the web which lies in the range from 2 to 10% of the length of the path of said light bead.

3. Hole seeking apparatus according to claim 2 and wherein said distance lies in the range from 4 to 6% of the length of the path of the said light bead.

4. Hole seeking apparatus according to claim 2 and wherein said distance amounts to substantially 5% of the length of the path of the said light bead.

5. Hole seeking apparatus according to claim 1 and wherein said first and second mirror wheels respectively have ten facets.

6. Hole seeking apparatus according to claim 1 and wherein said light receiving arrangement comprises a light conducting rod extending transversely across the web.

7. Hole seeking apparatus in accordance with any one of the preceding claims and wherein the slot aperture is a modal aperture stop which solely allows the zero order to reach the objective and which masks out all other orders.

8. Hole seeking apparatus for material webs comprising light source means for projecting a light beam onto mirror wheel means located optically in front of a concave mirror, whereby to produce a scanning beam in the image space of the concave mirror which periodically sweeps across a scanning path on the material web, and in which the mirror wheel means comprises two substantially identical multiply faceted mirror wheels which lie coaxially on one another and are displaced by a half pitch of one facet relative to one another, and wherein said light beam forms an illuminated patch of light on both said first and second mirror wheels with the width of said patch of light in the peripheral direction of the first and second mirror wheels being less than one half the peripheral length of any single facet and such that edges between the facets of the first and second mirror wheels first enter the patch of light when the light bead on the web is at a distance from the margin of the web such that light scattered from said edge within the scattering lobe of the edge will not be reflected from said concave mirror past a margin of the material web.

* * * * *